United States Patent
Ciervo et al.

[11] Patent Number: 5,403,324
[45] Date of Patent: Apr. 4, 1995

[54] FLEXIBLE CATHETER WITH STONE BASKET AND ULTRASONIC CONDUCTOR

[75] Inventors: Donald J. Ciervo, Merrick; Ronald Fagan, Glen Oaks, both of N.Y.

[73] Assignee: Microsonic Engineering Devices Company, Inc., Merrick, N.Y.

[21] Appl. No.: 181,040

[22] Filed: Jan. 14, 1994

[51] Int. Cl.⁶ .............................................. A61N 7/00
[52] U.S. Cl. ................... 606/128; 606/127; 604/264
[58] Field of Search ................... 604/19, 22, 104–109, 604/264; 606/1, 110, 113, 127, 128, 205–207

[56] References Cited

U.S. PATENT DOCUMENTS

| | | | |
|---|---|---|---|
| 4,611,594 | 9/1986 | Grayhack et al. | 606/127 |
| 5,176,688 | 1/1993 | Narayan et al. | 606/127 |
| 5,190,557 | 3/1993 | Borodulin et al. | 606/128 |
| 5,197,968 | 3/1993 | Clement | 606/128 |
| 5,312,418 | 5/1994 | Bonnet | 606/128 |

FOREIGN PATENT DOCUMENTS 3525458  1/1987  Germany .......................... 606/128

Primary Examiner—Stephen C. Pellegrino
Assistant Examiner—Glen Dawson
Attorney, Agent, or Firm—Charles E. Baxley

[57] ABSTRACT

A flexible catheter which has a basket at one end for the capture and removal of a calculus, such as a kidney stone. The catheter includes a plurality of wires with ends forming a basket, an elongate flexible tube through which the wires pass, a handpiece supporting the tube and having a cavity, a shaft disposed in the cavity and fixedly connecting to second ends of the wires, the tube and shaft having aligned central bores, a conductor extending through the bores, and lock means for holding the shaft in a selective position.

6 Claims, 2 Drawing Sheets

FLEXIBLE CATHETER WITH STONE BASKET AND ULTRASONIC CONDUCTOR

FIELD OF THE INVENTION

The present invention relates to a flexible catheter, and more particularly to an invasive type flexible catheter having a basket at one end thereof to capture a calculus such as a kidney stone, and even more particularly to an invasive flexible catheter with a basket for capturing a calculus and ultrasonic apparatus for disintegrating same.

BACKGROUND OF THE INVENTION

A first prior art apparatus and method for removing a calculus includes a bathtub wherein a patient is seated in a pool of water and includes two transducers which are positioned to focus on the calculus and to emit compression waves on opposite sides of the patient. These waves are focused on the calculus, and the absorption of these waves by the calculus tends to fatigue the calculus. Microscopic cracks form both within and outside the calculus after each blast caused by a lithotriptor that connects to the transducers. As each blast damages the calculus, it is finally fragmented into various sized particles. In some cases, more than 1000 blasts are needed before the calculus can be completely broken down and flushed from the patient which can take a few hours. One problem with the first prior art method is that it can leave the patient with external bruises or in some cases, can cause the kidneys or other organs to bleed.

A second prior art method of calculus removal involves drinking by the patient of dissolving agents. One problem with this method is that it can only be successful if the stones are of a certain biological make-up.

A third prior art device and method can be used if the calculus is small enough to be removed with a catheter that has a fixed basket on the end thereof. This catheters basket has a plurality of wires, usually a group of four wires, which are configured in such a way as to form a basket that will grip the calculus at four possible points or surfaces. The wires which form the basket structure are relatively tiny wires that are twisted together, thereby creating a small flexible bundle of wires. The flexibility of the wire bundles helps grip a calculus with an irregular surface contour. One problem with this method is that it is not effective when attempting to remove relatively large stones.

A fourth prior art device can remove relatively large stones, which are too large to be removed by a basket. This fourth device has a catheter which has an alligator-shaped clip device that is located at the end thereof. This clip Call be manipulated to hold a calculus in its jaws. The calculus, which is too large to be removed, can be crushed into smaller fragments by a connecting control mechanism, which forces the alligator-shaped clip to clamp down and crush the calculus. These fragments,. if small enough, can then be flushed from the body, and the larger remaining fragments can be removed with a basket, or crushed a second time with the alligator-shaped clip. One problem with this fourth prior art device is that stones may be highly calcified, and in attempting to crush the calculus the alligator-shaped clip may bend and fracture, or cause the wires connected to the alligator-shaped clip to be stressed beyond their elastic limit and finally fracture. If this should occur, the specialist or practitioner has to surgically remove not only the fragments of the alligator-shaped clip or wires, but the undamaged calculus. Often, a patients health will indicate that performing such surgery is too risky.

A fifth prior art device has a catheter which has a sonic or ultrasonic wire that extends through the catheter. This fifth device can disintegrate various types of stones. Fracturing of these stones is accomplished because of the ability of the end of the sonic wire to hammer the calculus, like that of a jack hammer, or to erode the calculus by cavitation forces which are formed at the tip of the sonic wire. One problem with this fifth device is that it is not chosen for a lithotripsy procedure, because of the inherent nature of these wires to fracture due to heat-induced metal fatigue or because of the possibility that the wire will slip from its normal position and pass into an organ or vessel thereby complicating the whole procedure.

SUMMARY OF THE INVENTION

According to the present invention, a flexible catheter is provided which has an elongate tube with an elongate central bore and a plurality of elongate holes peripherally spaced and surrounding the central bore. The tube has a first end portion and a second end portion. A plurality of wires form an exterior basket adjacent to the tube first end portion and extends through the elongated peripherally spaced holes to the second end portion. A conductor for ultrasonic energy extends from the exterior basket and through the tube central bore to a hollow end piece fixedly connected to the handpiece and opening to a cavity. A plunger is disposed in the cavity and is fixedly connected to the plurality of wires. The plunger is displaceably with the wires relative to the handpiece and the tube between a rearward position and a forward position. The plunger has an elongate central bore aligned with the tube central bore to receive the conductor, with lock means for holding the plunger in a fixed position relative to the handpiece.

It is therefore a principal object of the present invention to provide a catheter for use with an ultrasonic lithotripter.

Another object of the present invention is to provide an ultrasonic lithotripter catheter which minimizes friction, heat generation and conductor breakage.

A further object of the present invention is to provide an ultrasonic lithotripter catheter which can receive a cooling fluid for minimizing friction and heat conductor breakage or which can receive a contrast medium, or a dissolving agent.

Still another object of the present invention is to provide a catheter having a basket which is longitudinally displaceable for capturing a calculus and for aligning the calculus with an adjacent tube central bore.

BRIEF DESCRIPTION OF THE DRAWINGS

The foregoing and other objects and many of the attendant advantages of this invention will be readily appreciated as the same becomes better understood by reference to the following detailed description when considered in connected with the accompanying drawings in which.

DESCRIPTION OF THE PREFERRED EMBODIMENT

Figure 1:
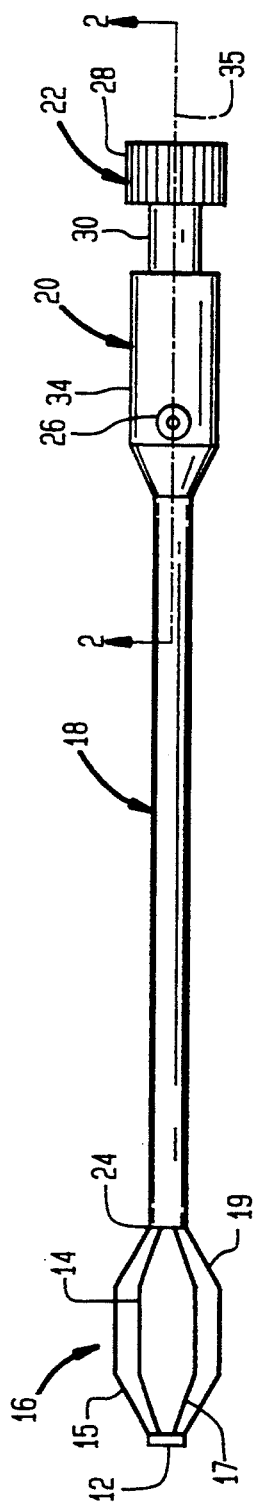
FIG. 1 is a plan view of a lithotripsy catheter according to this invention.

Referring now to the drawings, wherein like reference characters designated like or corresponding parts throughout, there is illustrated in FIG. 1 a lithotripsy catheter generally designated 10 with a far or distal end 12 having a basket generally designated 16 made of wires 14, 15, 17, 19 for capturing a calculus (not shown). The catheter 10 has a catheter tube generally desgniated 18 which is flexible in order to provide flexibility when performing lithotripsy procedures. A near or rear end 20 of the catheter 10 has a control mechanism 22 which is intended to allow a practitioner to manipulate the basket 16 in and out of the catheter tube 18 thereby providing correct positioning of a calculus (not shown) against a catheter tip 24.

The control mechanism 22 contains a syringe fitting 26 which allows a contrast medium or cooling liquid to pass through the catheter tube 18 and to pass into the area of the basket 16. The control mechanism 22 also contains a control knob 28 which is permanently fixed to a control shaft 30. Connected to the control shaft 30 are one end of each of the basket wires 14, 15, 17, 19 which make up the basket 16 of the lithotripsy catheter 10.

Figure 2:
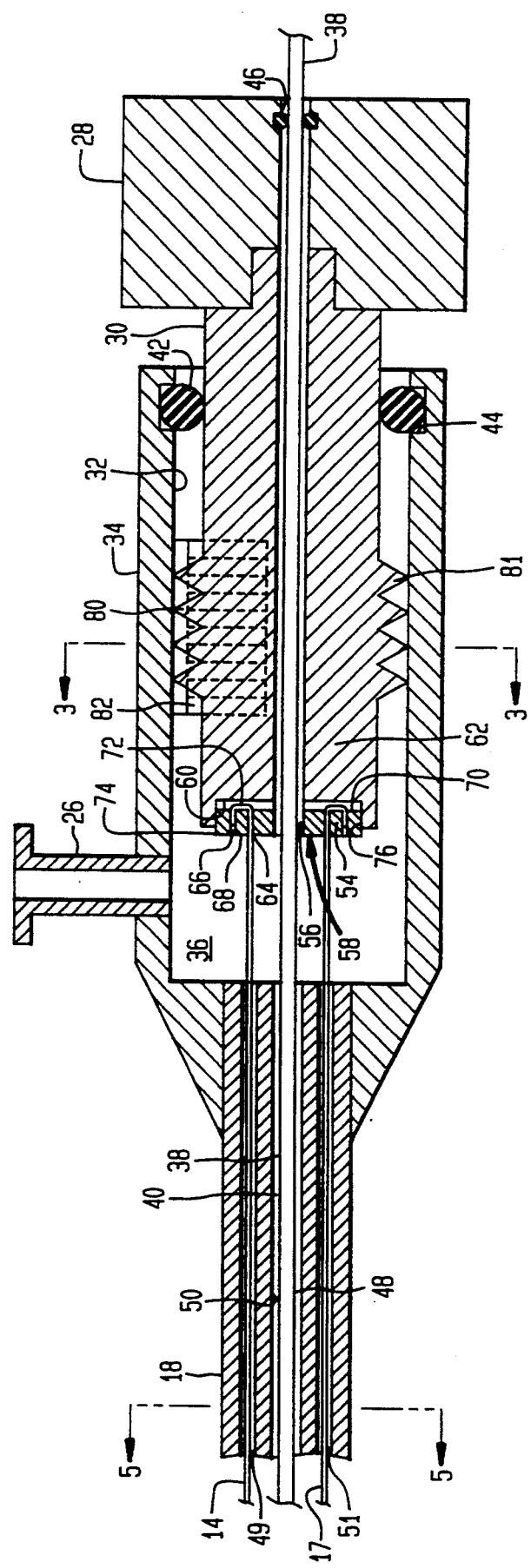
FIG. 2 is a sectional view taken along line 2—2 of FIG. 1.

In operation, in order to capture a calculus, the control knob 28 is rotated, a quarter turn until positioned properly. The control shaft 30, which is located within a longitudinally extending groove or cavity 32, as shown in FIG. 2, is disposed inside a handpiece 34, such that the control shaft 30 can now move the basket wires 14, 15, 17, 19 in and out of the catheter tube 18. At this time, the control shaft 30 can be pushed into the handpiece 34 along the handpiece axis 35, and the control knob 28 operated to open the basket 16. The calculus can then be captured and fished toward the catheter tip 24 by pulling the control knob 28 out from within the handpiece 34 until the calculus is firmly held against the catheter tip 24. Restraining the calculus is accomplished by turning the control knob 28 clockwise a quarter turn thereby locking control shaft 30 into position.

FIG. 2 shows a fluidic reservoir 36, which is disposed inside the handpiece 34. To overcome the problem of ultrasonic wire fatigue within the catheter 10, the catheter 10 is equipped with a fluidic reservoir 36 which allows a liquid cooling solution to be passed over a hot or heated ultrasonic conductor or wire 38 by way of a central bore or lumen 40 formed as part of the catheter tube 18. In order to prevent leakage between the control shaft 30 and the handpiece 34, a liquid sealing means 42 may be provided which may be in the form of an O-ring, that fits in a groove 44. Another O-ring 46 is also provided, which seals the catheter 10 within control knob 28, thereby preventing leakage of fluids that may reduce the efficiency or performance of the ultrasonic wire 38. With the O-ring 46, fluid pressure is maintained within the central lumen 40 providing a fluidic barrier between an outer surface 48 of the ultrasonic wire 38 and an inside surface 50 of the center lumen 40, thereby preventing the ultrasonic wire 38 from transforming into a transverse vibrating element which may lead to wire breakage. Another means of preventing metal fatigue of the ultrasonic wire 38 is to fabricate all surfaces coming into contact with the vibrating ultrasonic wire 38 from plastic material or the like, which minimizes friction and provides isolation from any metallic materials that may cause pitting of the ultrasonic wire 38 during lithotripsy procedures and prevents the basket wires 14, 15, 17 and 19 from contacting the ultrasonic wire 38. The catheter tube 18 has relatively small holes 49, 50, 51, 52, disposed near its outer surface or circumference. These smaller holes 49, 50, 51, 52, also surround the central lumen 40, such that all energy emitting portions or devices are centrally located within the catheter 10, whereby correct positioning of the calculus is facilitated. The control shaft 30, the control knob 28 and a fixture plate 54 of a coupling means 58 are also made of a plastic material and contain an aligned central lumen 56 which protects the ultrasonic wire 38 from metal fatigue during lithotripsy procedures. A wire fixture plate 54 is adapted to be seated or tightly fitted in a recess 60 at one end 62 of the control shaft 30.

The coupling means or connection means 58 prevents ultrasonic wire 38 from contacting metallic materials such as the basket wires 14. The coupling means 58 also attach the basket wires 14 to the plastic control shaft 30. The coupling means 58, which fit into a recess 60, at a shaft end 62, transmit the forces applied by the basket wires 14, to control the control shaft 30.

The coupling means 58 include the wire fixture plate 54, which is securely connected to the control shaft 30 and which maintains basket wires 14 in position when operating the catheter 10. The wire fixture plate 54 has two typical holes 64 and 66 for the typical basket wire 14 that is secured to the control shaft 30. There are a total of eight holes or two holes for each of the four wires 14, 15, 17, 19. The typical first hole 64 extends between front end 68 and a rear end 70 of the wire fixture plate 54, and is used to pass the basket wire 14 through the hole 64 in the wire fixture plate 54. After all of the basket wires 14, 15, 17, 19 are passed respectively through the first holes 64, the ends of the basket wires are each bent to form a hook or loop wire 72. Then, the loop wire 72 is inserted through the typical second hole 66 within the wire fixture plate 54. When complete, the loop wire 72 is placed into the second hole 66 within the wire fixture plate 54 for each of the basket wires 14, 15, 17, 19 used to make the basket end 16. After all of the basket wires 14, 15, 17, 19 are within their designated locations within the wire fixture plate 54, the wire fixture plate 54 is then permanently coupled as by bonding into the control shaft 30 along the outer surfaces 74 of the wire fixture plate 54, and the inner surface 76 of the recess 60 of the control shaft 30 for the proper fit and surface area contact needed to provide reliability.

Figure 3:
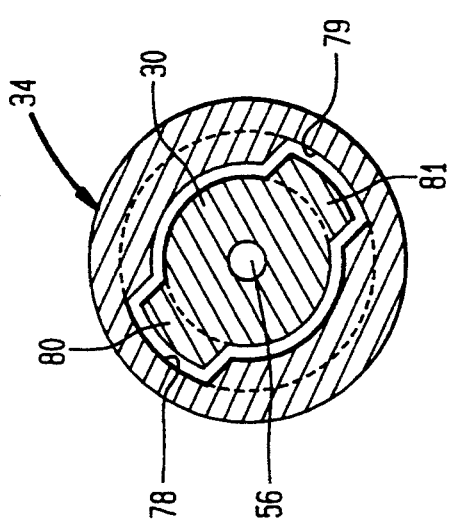
FIG. 3 is a sectional view taken along line 3—3 of FIG. 2.

FIG. 3 shows the handpiece 34 and the control shaft 30 in a first position for capturing a calculus and for maintaining a secure hold over the calculus. To allow the basket 16, as shown in FIG. 1, to adjust to the contour of irregular calculus surfaces, the handpiece 34 is broached with two grooves 78, 79 such that the control shaft 30 can slide longitudinally in and out of the grooves 78, 79. The control shaft 30 has threaded portions 80, 81 that fit into threaded portions 82, 83 of the handpiece 34, like that of a key. The threaded portion 80, 81 of the control shaft 30 remain within the boundaries of the bracket or slotted portions 78, 79 of the handpiece 34 for complete extension or elongation and for withdrawal or contraction of the basket 16. To lock the basket wires 14 into position for gripping the calculus, the control shaft 30, is pulled out from within the handpiece 34, thereby directing the basket wires into the catheter tube 18.

Figure 4:
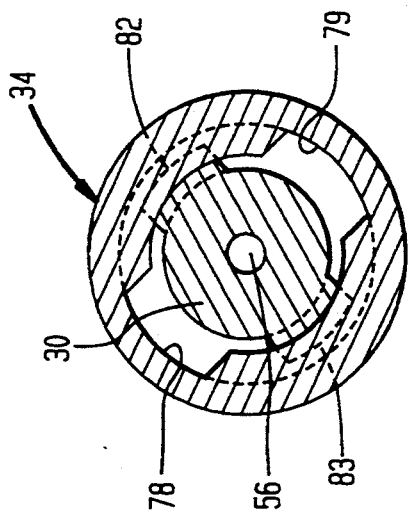
FIG. 4 is a sectional view corresponding to FIG. 3, where a catheter portion is angularly displaced.

As shown in FIG. 4, the control shaft 30 is then turned clockwise one quarter turn to allow threaded portions 80, 81 of the control shaft 30 to locate within the threaded portions 82, 83 of the handpiece 34, thereby securing the calculus into position. To release the grip applied to the calculus, the control shaft 30 is turned counterclockwise within the handpiece 34, thereby releasing the coupling between the threaded portions 80, 81 of the control shaft 30 and the threaded portions 82, 83 of the handpiece 34, so that the threaded portions 80, 81 of the control shaft 30 are in alignment with the respective broached grooves 78, 79 of the handpiece 34. Pushing the control shaft 30 into the handpiece 34 opens the basket end of the catheter 10 and releases the calculus.

The central lumen 56 of the plastic control shaft 30 protects devices or wires placed into the catheter 10. This central lumen 56 can direct a laser or ultrasonic wire directly to the tube 18 to facilitate lithotripsy procedures and to remove the high risk associated with these devices.

Figure 5:
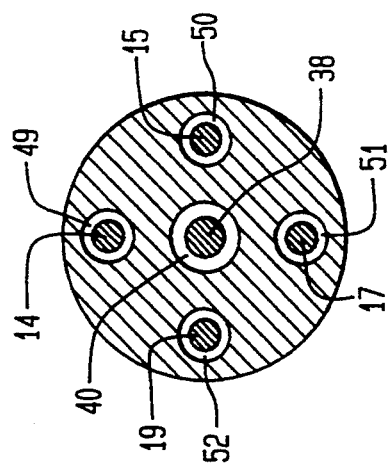
FIG. 5 is a sectional view taken along line 5—5 of FIG. 2.

As shown in FIG. 5, the wire holes or lumens 49, 50, 51, 52, are disposed around the central lumen 40, so as to provide correct positioning of a calculus against the catheter tip 24, of the catheter 10.

Advantages of catheter 10 are:

(a) A major advantage of the catheter 10 over prior art catheters, for use in extracting a calculus, is the ability of the catheter 10 to keep a definite central location relative to the calculus, thereby directing a high energy source directly into the calculus, and not along a line which is tangent to the calculus and which Could be directly in line with a vessel or an organ.

(b) The controlled protrusion of ultrasonic wire 38 from the catheter tip 24 of the catheter 10 minimizes the possibility that the energized tip 24 may damage tissue or organs.

(c) The catheter 10 facilitates lithotripsy procedures allowing the practitioner to grasp the handpiece of the catheter 10 with one hand as the basket 16 firmly grasps the calculus within the flexible wires 14, 15, 17, 19 by use of the control mechanism 22, and allows the other hand to maneuver the energy source against the calculus but within the confinement of the central lumen 40 of the catheter 10.

It should be understood that the foregoing description relates to only a preferred embodiment of the invention, which has been by way of example only, and that it is intended to cover all changes and modifications of the example of the invention herein chosen for the purposes of the disclosure, which do not constitute departures from the spirit and scope of the invention.

What is claimed:

1. A flexible catheter, comprising:

a plurality of wires having first end portions forming a basket which expands in a forward position and contracts in a rearward position;

an elongate flexible tube having a plurality of elongate peripherally spaced holes through which second ends of said respective wires pass;

a handpiece having an end portion supporting said tube and having an elongate cavity;

a shaft disposed in said cavity and having an end portion displaceable relative to said handpiece and said tube;

connecting means fixedly connecting an end portion of said shaft to second end portions of said wires;

said tube and said shaft having aligned central bores;

a conductor extending through said central bores from said basket to a region outside said central bores; and a lock means for holding said shaft and said basket in a selective position relative to said handpiece and said tube.

2. A catheter as claimed in claim 1, wherein said handpiece has a fitting opening into said cavity for depositing or removing a liquid in said cavity, said wire holes and a region around said basket.

3. A catheter as claimed in claim 1, wherein said lock means includes an arcuate threaded portion mounted on said shaft and a cooperating arcuate threaded portion mounted on the handpiece, said threaded portions being disposed in said cavity.

4. A catheter as claimed in claim 1, wherein said tube and said shaft are made of plastic material.

5. A catheter as claimed in claim 1, wherein said connecting means include:

a fixture plate having a plurality of pairs of holes respectively receiving said second end portions of said wires;

each of said wire second end portions having a hook portion received in a respective pair of holes;

said fixture plate being fixedly connected to said shaft end portion.

6. A catheter as claimed in claim 1, including first seal means disposed between said shaft and said handpiece for sealing said cavity; and second seal means disposed between said conductor and a knob on said shaft for sealing said shaft central bore and said cavity.

* * * * *